US012733976B2

(12) United States Patent
Tschida et al.

(10) Patent No.: US 12,733,976 B2
(45) Date of Patent: Sep. 15, 2026

(54) DEVICES, SYSTEMS, AND METHODS FOR SIMULTANEOUS LIQUID INFUSION AND CATHETER MOTION

(71) Applicant: KONINKLIJKE PHILIPS N.V., Eindhoven (NL)

(72) Inventors: Adam Tschida, Greenfield, MN (US); James David Cezo, Colorado Springs, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1342 days.

(21) Appl. No.: 17/298,780

(22) PCT Filed: Nov. 27, 2019

(86) PCT No.: PCT/EP2019/082772

§ 371 (c)(1),
(2) Date: Jun. 1, 2021

(87) PCT Pub. No.: WO2020/114861

PCT Pub. Date: Jun. 11, 2020

(65) Prior Publication Data

US 2022/0031393 A1 Feb. 3, 2022

Related U.S. Application Data

(60) Provisional application No. 62/774,274, filed on Dec. 2, 2018.

(51) Int. Cl.
*A61B 18/24* (2006.01)
*A61B 18/00* (2006.01)

(52) U.S. Cl.
CPC .... *A61B 18/24* (2013.01); *A61B 2018/00166* (2013.01); *A61B 2018/00345* (2013.01); *A61B 2218/002* (2013.01)

(58) Field of Classification Search
CPC ............. A61B 2218/002; A61B 18/24; A61M 25/0113; A61M 25/0136; A61M 5/1452
See application file for complete search history.

(56) References Cited

U.S. PATENT DOCUMENTS 4,529,399 A 7/1985 Groshong
5,456,684 A * 10/1995 Schmidt ................ A61M 1/772 606/174

(Continued)

FOREIGN PATENT DOCUMENTS

| EP | 0125843 | 11/1984 |
|---|---|---|
| WO | 2011/008922 | 1/2011 |

OTHER PUBLICATIONS

International Search Report and Written Opinion Dated Feb. 26, 2020 For International Application No. PCT/EP2019/082772 Filed Nov. 27, 2019.

*Primary Examiner* — Emily L Schmidt
*Assistant Examiner* — Samuel J Marrison

(57) ABSTRACT

A vascular treatment system includes a vascular treatment device configured to be disposed within a treatment space of a subject. The system further includes an actuation device operatively coupled to the vascular treatment device. The actuation device includes a movement actuator operatively coupled to the vascular treatment system. The movement actuator is actuatable to move the vascular treatment device within the treatment space. The actuation device further includes a liquid reservoir carrying a liquid, and a liquid infusion actuator operatively coupled to the liquid reservoir. The liquid infusion actuator is actuatable to deliver the liquid from the liquid reservoir to the treatment space via the vascular treatment device. The device further includes a user input actuatable to simultaneously actuate the movement actuator and the liquid infusion actuator.

16 Claims, 6 Drawing Sheets

(56) References Cited

U.S. PATENT DOCUMENTS

2003/0004460 A1* 1/2003 Bedell ................ A61B 1/00105 604/95.04
2007/0135733 A1* 6/2007 Soukup ............ A61M 25/0136 604/95.04
2008/0009875 A1 1/2008 Sankaran
2009/0182314 A1* 7/2009 Eliachar ................ A61B 18/24 606/15
2016/0184022 A1 6/2016 Grace
2016/0184023 A1 6/2016 Grace
2016/0329685 A1 11/2016 Katsura
2017/0080157 A1* 3/2017 Cabiri ................ A61M 5/31511
2017/0333132 A1 11/2017 Grace
2018/0008348 A1 1/2018 Grace
2018/0250015 A1 9/2018 Koo
2018/0265942 A1 9/2018 Zhao

* cited by examiner 206
202
208
204
214
212
216
210
200

302
304
P
312
306
308
300
310

500
502
504
506
508
510
512
514

DEVICES, SYSTEMS, AND METHODS FOR SIMULTANEOUS LIQUID INFUSION AND CATHETER MOTION

CROSS-REFERENCE TO RELATED APPLICATION

This application is the U.S. National Phase application under 35 U.S.C. § 371 of International Application No. PCT/EP2019/082772 filed Nov. 27, 2019, which claims the benefit of U.S. Provisional Patent Application No. 62/774,274 filed Dec. 2, 2018. These applications are hereby incorporated by reference herein.

FIELD OF THE DISCLOSURE

The devices, systems, and methods described herein generally relate to vascular surgical procedures that include liquid infusion and catheter use, and more specifically relate to surgical procedures that include simultaneous liquid infusion to a patient and catheter motion within the patient.

BACKGROUND

Some surgical procedures include simultaneous liquid infusion to a patient and catheter translation within the patient. For example, laser atherectomy procedures typically involve simultaneous saline infusion to a patient and laser catheter translation within the patient. Generally, these procedures involve actuating a syringe carrying a liquid while advancing the catheter within the patient. It is relatively difficult for a single user (for example, a surgeon) to perform these actions simultaneously. Accordingly, a single user (for example, a first surgeon) typically actuates the syringe while a second user (for example, a second surgeon) advances the catheter within the patient. However, this approach requires considerable coordination and communication between the users to ensure that liquid delivery and catheter translation occur at appropriate rates.

Further, syringe actuation relies on the ability of the user to apply sufficient pressure to generate an appropriate flow rate. If the viscosity of the liquid is relatively high and/or the liquid is delivered via a relatively narrow passageway (for example, between the catheter and an introducer through which the catheter extends), the resulting pressure can be too great for the user to reach the desired flow rate using a syringe. In these situations, user typically turns to a powered infusion system. However, such infusion systems are not available in all settings and are typically viewed as being cost prohibitive.

Accordingly, it is desirable to provide improved devices, systems, and methods that facilitate simultaneously delivering a liquid to a treatment space and moving a catheter in the treatment space during a vascular surgical procedure.

SUMMARY

The present disclosure presents a vascular treatment system that includes a vascular treatment device configured to be disposed within a treatment space of a subject. The system further includes an actuation device operatively coupled to the vascular treatment device. The actuation device includes a movement actuator operatively coupled to the vascular treatment device. The movement actuator is actuatable to move the vascular treatment device within the treatment space. The actuation device further includes a liquid reservoir carrying a liquid, and a liquid infusion actuator operatively coupled to the liquid reservoir. The liquid infusion actuator is actuatable to deliver the liquid from the liquid reservoir to the treatment space via the vascular treatment device. The device further includes a user input actuatable to simultaneously actuate the movement actuator and the liquid infusion actuator.

The device according to the previous paragraph, wherein the vascular treatment device includes an introducer sheath having an inner lumen, and a catheter translatably carried in the inner lumen of the introducer sheath.

The device according to any of the previous paragraphs, wherein the catheter is a laser catheter.

The device according to any of the previous paragraphs, wherein the catheter includes a distal end configured to be disposed in the treatment space, and the actuation device further includes an indicator configured to indicate a position of the distal end of the catheter relative to the actuation device.

The device according to any of the previous paragraphs, wherein the actuation device further includes a housing, the user input is a trigger, and the trigger is translatably actuatable relative to the housing to simultaneously actuate the movement actuator and the liquid infusion actuator.

The device according to any of the previous paragraphs, wherein the movement actuator includes an arm coupling the trigger to the vascular treatment device.

The device according to any of the previous paragraphs, wherein the actuation device further includes a housing, the user input is a lever, and the lever is rotatably actuatable relative to the housing to simultaneously actuate the movement actuator and the liquid infusion actuator.

The device according to any of the previous paragraphs, wherein the liquid reservoir includes a syringe chamber carrying the liquid, and the liquid infusion actuator includes a piston movably carried within the syringe chamber.

The present disclosure presents an actuation device for a vascular treatment system. The actuation device includes a movement actuator configured to be operatively coupled to a vascular treatment device. The movement actuator is actuatable to move the vascular treatment device within a treatment space of a subject. The actuation device further includes a liquid reservoir carrying a liquid, and a liquid infusion actuator operatively coupled to the liquid reservoir. The liquid infusion actuator is actuatable to deliver the liquid from the liquid reservoir to the treatment space via the vascular treatment device. The actuation device further includes a user input actuatable to simultaneously actuate the movement actuator and the liquid infusion actuator.

The device according to the previous paragraph, further including an indicator configured to indicate a position of the vascular treatment device relative to the actuation device.

The device according to any of the previous paragraphs, further including a housing, wherein the user input is a trigger, and the trigger is translatably actuatable relative to the housing to simultaneously actuate the movement actuator and the liquid infusion actuator.

The device according to any of the previous paragraphs, wherein the movement actuator includes an arm configured to couple the trigger to the vascular treatment device.

The device according to any of the previous paragraphs, further including a housing, wherein the user input is a lever, and the lever is rotatably actuatable relative to the housing to simultaneously actuate the movement actuator and the liquid infusion actuator.

The device according to any of the previous paragraphs, wherein the liquid reservoir includes a syringe chamber carrying the liquid, and the liquid infusion actuator includes a piston movably carried within the syringe chamber.

The present disclosure presents a vascular treatment system including a vascular treatment device configured to be disposed within a treatment space of a subject. The system further includes an actuation device operatively coupled to the vascular treatment device. The actuation device includes a movement actuator operatively coupled to the vascular treatment device. The movement actuator is actuatable to move the vascular treatment device within the treatment space. The actuation device further includes a liquid infusion actuator configured to operatively couple to a liquid reservoir. The liquid infusion actuator is actuatable to deliver a liquid from the liquid reservoir to the treatment space via the vascular treatment device. The actuation device further includes a user input being actuatable to simultaneously actuate the movement actuator and the liquid infusion actuator.

The present disclosure presents an actuation device for a vascular treatment system, and the actuation device includes a movement actuator configured to be operatively coupled to a vascular treatment device. The movement actuator is actuatable to move the vascular treatment device within a treatment space of a subject. The actuation device further includes a liquid infusion actuator configured to operatively couple to a liquid reservoir. The liquid infusion actuator is actuatable to deliver a liquid from the liquid reservoir to the treatment space via the vascular treatment device. The actuation device further includes a user input being actuatable to simultaneously actuate the movement actuator and the liquid infusion actuator.

The phrases “at least one”, “one or more”, and “and/or” are open-ended expressions that are both conjunctive and disjunctive in operation. For example, each of the expressions “at least one of A, B and C”, “at least one of A, B, or C”, “one or more of A, B, and C”, “one or more of A, B, or C” and “A, B, and/or C” means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

The term “a” or “an” entity refers to one or more of that entity. As such, the terms “a” (or “an”), “one or more” and “at least one” may be used interchangeably herein. It is also to be noted that the terms “comprising”, “including”, and “having” may be used interchangeably.

The term “means” as used herein shall be given its broadest possible interpretation in accordance with 35 U.S.C. Section 112(f). Accordingly, a claim incorporating the term “means” shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
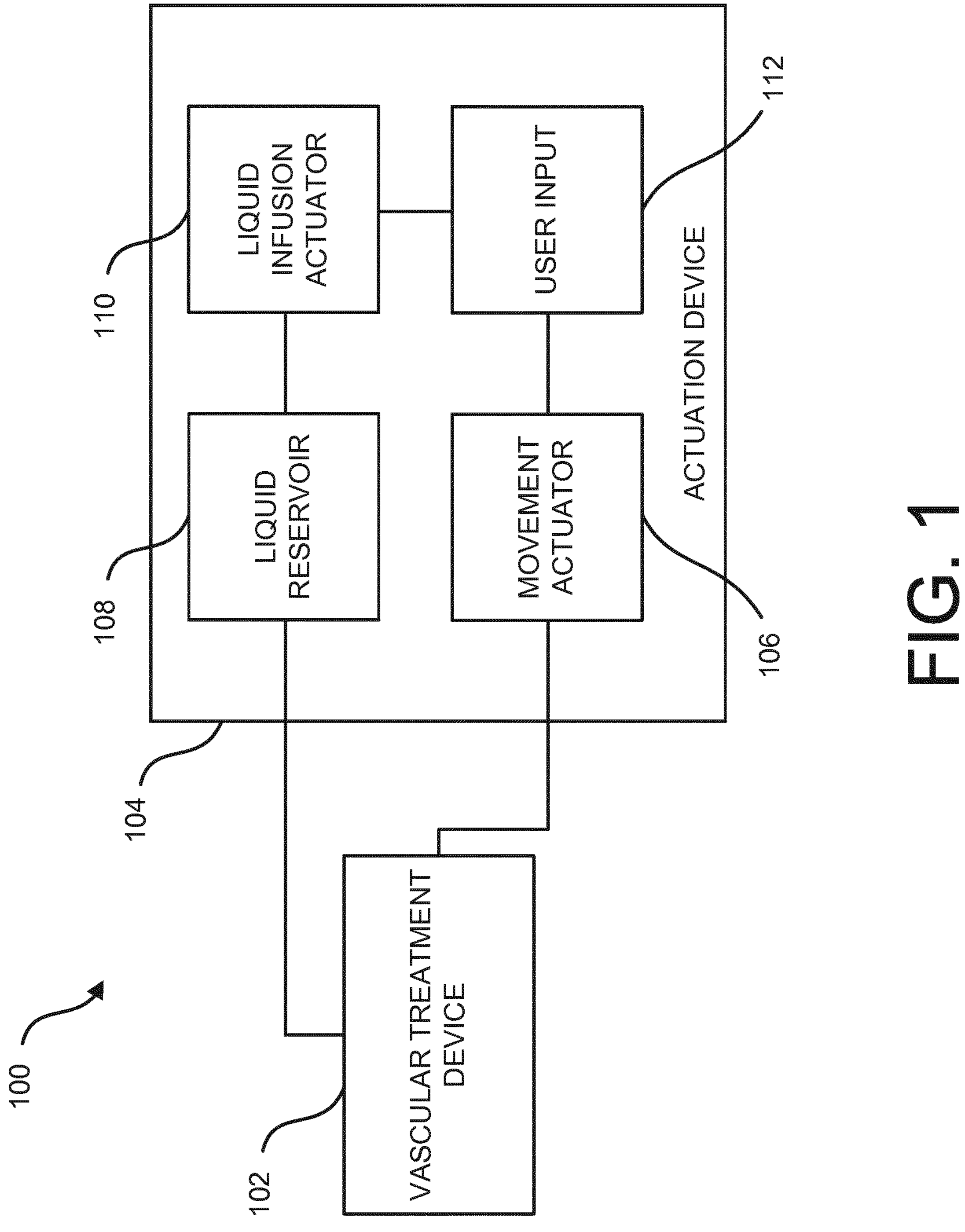
FIG. 1 is a schematic illustration of a vascular treatment system according to an embodiment of the present disclosure.

The present disclosure relates generally to devices, systems, and methods that facilitate simultaneously delivering a liquid to a treatment space (for example, a lumen or cavity in the vasculature of a subject, such as a patient) and moving a catheter in the treatment space during a vascular surgical procedure. FIG. 1 illustrates a vascular treatment system 100 according to an embodiment of the present disclosure. The vascular treatment system 100 generally includes a vascular treatment device 102 that is configured to be disposed within a treatment space and provide treatment to a subject during a vascular surgical procedure. The vascular treatment device 102 is operatively coupled to an actuation device 104 that is configured to be disposed externally to the subject and manipulated by a user (for example, a surgeon). The actuation device 104 includes a movement actuator 106 that is operatively coupled to and facilitates movement of the vascular treatment device 102 within the treatment space. The actuation device 104 also includes a liquid reservoir 108 and a liquid infusion actuator 110 that are operatively coupled to the vascular treatment device 102 and facilitate delivery of a liquid to the treatment space via the vascular treatment device 102. The actuation device 104 includes a user input 112 that may be actuated by a user to facilitate simultaneous actuation of the movement actuator 106 and the liquid infusion actuator 110, and the actuation device 104 thereby moves the vascular treatment device 102 within the treatment space and delivers a liquid to the treatment space via the vascular treatment device 102. Detailed examples of the above components are described below.

Vascular treatment devices forming part of systems according to embodiments of the present disclosure may take various forms. Generally, vascular treatment devices according to some embodiments of the present disclosure include an introducer or delivery sheath, a treatment catheter that is translatably carried within and extendable from the introducer sheath, and a guidewire. As a more specific example and referring to FIG. 2, an exemplary embodiment of a vascular treatment device 200 is illustrated. The vascular treatment device 200 includes an introducer or delivery sheath 202, a laser catheter 204 that is translatably received within a lumen 206 of the introducer sheath 202 and extendable from a distal end 208 of the introducer sheath 202, and a guidewire 210 that is translatably received within a lumen 212 of the laser catheter 204 and along which the laser catheter 204 translates to reach the treatment space. The laser catheter 204 couples to a laser generator (not shown—such as, for example, the Spectranetics CVX-300® Excimer Laser System, which is available from the Koninklijke Philips N.V.), receives laser energy therefrom, and emits the laser energy to treat tissue and/or other materials (for example, an occlusion) within the treatment space of the subject. The laser catheter 204 may be or may be similar to, for example, any Spectranetics laser catheters available from Koninklijke Philips N.V. Such laser catheters include, for example, those available under the tradenames ELCA™ and Turbo Elite™ (each of which is used for coronary intervention or peripheral intervention, respectively, such as recanalizing occluded arteries, changing lesion morphology, and facilitating stent placement) and SLSII™ and GlideLight™ (which is used for surgically implanted lead removal). The working (distal) end 214 of the laser catheter 204 may have a plurality of laser emitters 216 (for example, optical fibers) that emit the laser energy received from the laser generator and ablate the targeted tissue and/or other materials within the treatment space. The opposite (proximal) end of the laser catheter 204 may have a fiber optic coupler (not shown) for coupling the laser catheter 204 to the laser generator. In these embodiments and others, the liquid carried in the liquid reservoir and delivered to the treatment space may be saline. The liquid reservoir may be in fluid communication with the lumen 206 of the introducer sheath 202, and the liquid reservoir may deliver the liquid to the treatment space via the lumen 206 of the introducer sheath 202.

Figures 2, 3:
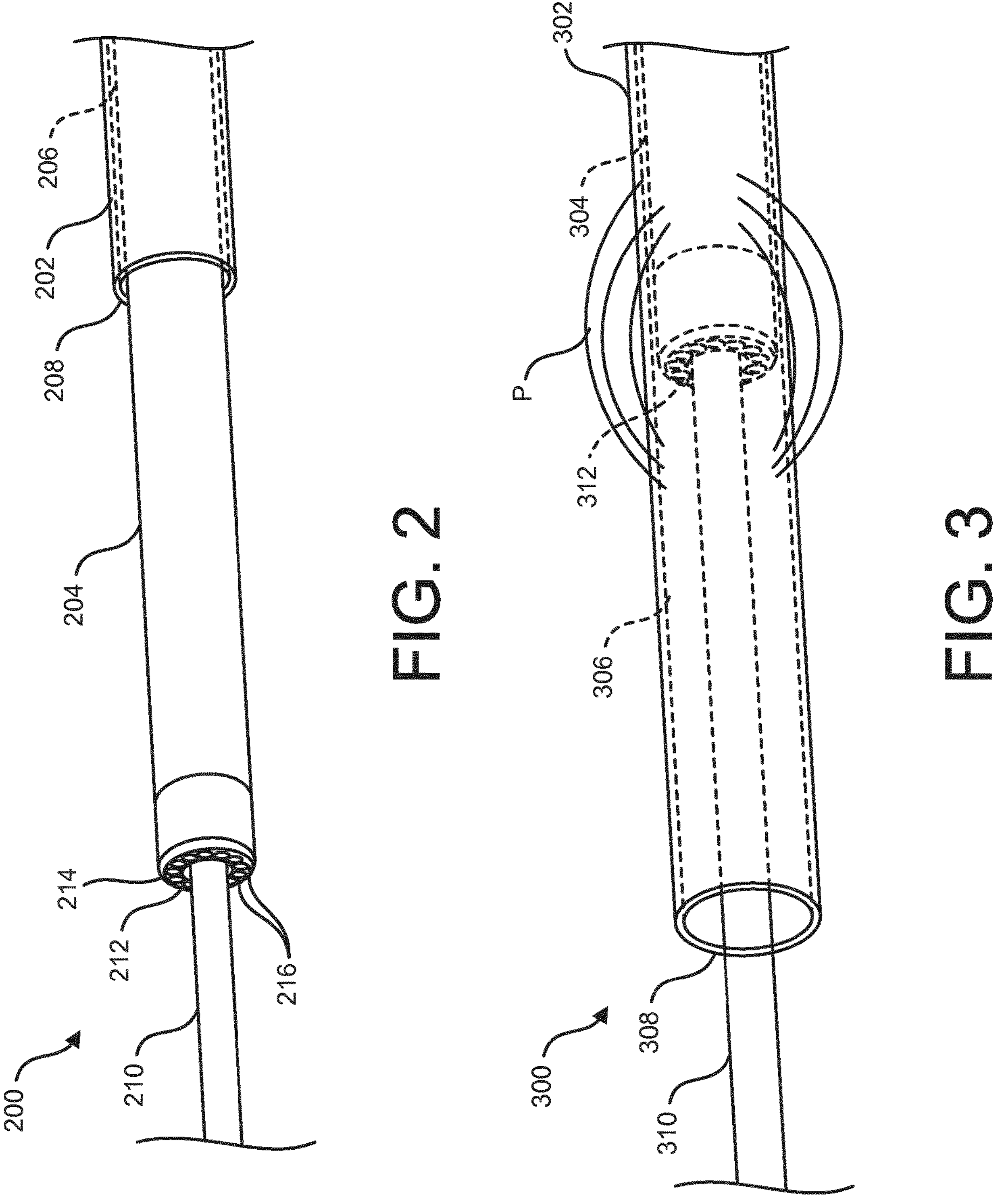
FIG. 2 is a perspective partial view of an exemplary vascular treatment device of vascular treatment systems according to embodiments of the present disclosure.
FIG. 3 is a perspective partial view of another exemplary vascular treatment device of vascular treatment systems according to embodiments of the present disclosure.

FIG. 3 illustrates another specific exemplary embodiment of a vascular treatment device 300. The vascular treatment device 300 includes an introducer or delivery sheath 302, a laser catheter 304 that is translatably carried within a lumen 306 of the introducer sheath 302 and extendable from a distal end 308 of the introducer sheath 302, and a guidewire 310 that is translatably received within a lumen 312 of the laser catheter 304 and along which the laser catheter 304 translates to reach the treatment space. The introducer sheath 302 may be or may be similar to, for example, any of the introducer sheaths (also referred to as "outer sheaths") described in the patent documents listed below. The laser catheter 304 may be or may be similar to, for example, any of the laser catheters described in the patent documents listed below.

Further, the introducer sheath 302, the laser catheter 304, and the guidewire 310 may generally be used to facilitate treatment within a treatment space in the same or similar manners to any of those described in the patent documents listed below (particularly, to emit laser energy into contrast solution to thereby generate pressure waves P for disrupting vascular occlusions, fracturing intraluminal calcium deposits, and/or fracturing medial calcium deposits). In these embodiments and others, the liquid carried in the liquid reservoir and delivered to the treatment space may be contrast medium or contrast solution, as described in the patent documents listed below. The liquid reservoir may be in fluid communication with the lumen 306 of the introducer sheath 302, and the liquid reservoir may deliver the liquid to the treatment space via the lumen 306 of the introducer sheath 302. The following patent documents are hereby incorporated herein by reference in their entireties for all that they teach and for all purposes: U.S. application Ser. No. 14/984,308, filed Dec. 30, 2015, entitled Laser-Induced Pressure Wave Emitting Catheter Sheath; U.S. application Ser. No. 14/984,050, filed Dec. 30, 2015, entitled Laser-Induced Fluid Filled Balloon Catheter; U.S. application Ser. No. 15/476,183, filed Mar. 31, 2017, entitled Laser-Induced Fluid Filled Balloon Catheter; U.S. application Ser. No. 15/659,064, filed Jul. 25, 2017, entitled Laser-Induced Pressure Wave Emitting Catheter Sheath; and U.S. application Ser. No. 15/659,402, filed Jul. 25, 2017, entitled Liquid Laser-Induced Pressure Wave Emitting Catheter Sheath.

Figure 4:
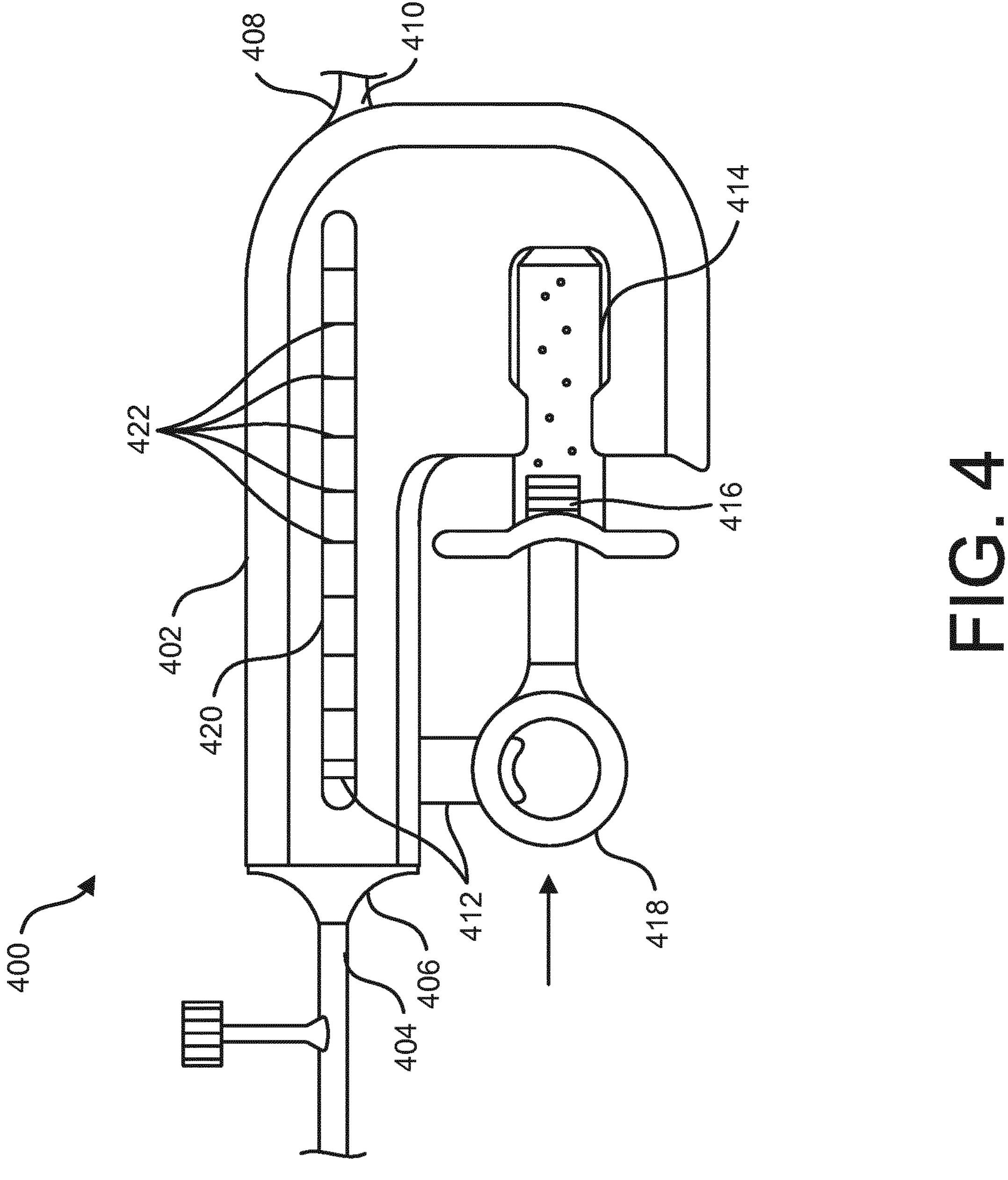
FIG. 4 is a side view of an exemplary actuation device of vascular treatment systems according to embodiments of the present disclosure.

As briefly described above, actuation devices according to embodiments of the present disclosure facilitate simultaneous movement of the vascular treatment device within the treatment space and delivery of a liquid to the treatment space via the vascular treatment device. Such actuation devices may take various forms. As a specific example and referring to FIG. 4, an exemplary embodiment of an actuation device 400 is illustrated. The actuation device 400 includes a housing 402 that is configured to be grasped by a user during a vascular surgical procedure. The housing 402 couples to an introducer sheath 404 at a first end 406. The introducer sheath 404 translatably carries a catheter (shown elsewhere), and the catheter extends through the housing 402 and outwardly from a port 408 at a second end 410 (for example, to facilitate coupling the catheter to a laser generator). The housing 402 translatably carries a movement actuator, more specifically an arm 412, that is coupled to the catheter within the housing 402. The housing 402 further carries a liquid reservoir, more specifically a syringe chamber 414, that carries a liquid and is in fluid communication with the introducer sheath 404. The syringe chamber 414 translatably carries a liquid infusion actuator, more specifically a piston 416. The piston 416 and the arm 412 both couple to a user input, more specifically a trigger 418, that is actuated by translating toward the second end 410 of the housing 402. As such, actuation of the trigger 418 causes simultaneous movement of the catheter relative to the introducer sheath 404 within the treatment space (specifically, proximally relative to the introducer sheath 404) and delivery of the liquid from the syringe chamber 414 to the treatment space via the introducer sheath 404. In some embodiments, the actuation device 400 includes an indicator for indicating the position of the distal end of the catheter. For example and as illustrated, the indicator may include an opening 420 that shows the position of the arm 412 within the housing 402 and relative to a plurality of demarcations 422. In some embodiments and as illustrated, the housing 402 may be shaped and the trigger 418 and the syringe chamber 414 may be positioned such that the actuation device 400 generally has a pistol-like appearance.

Figures 5A, 5B:
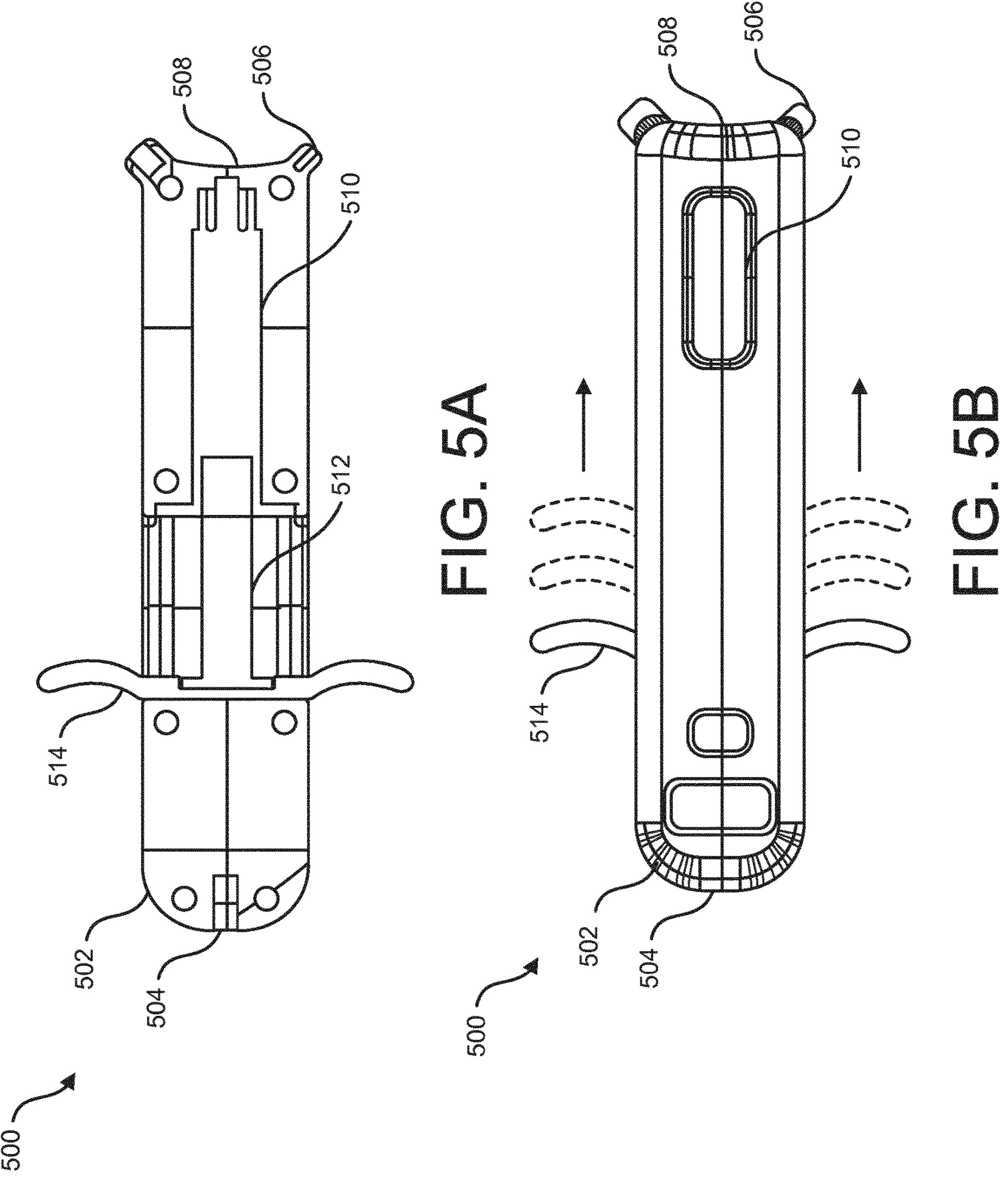
FIG. 5A is a longitudinal sectional view of another exemplary actuation device of vascular treatment systems according to embodiments of the present disclosure.
FIG. 5B is a side view of the actuation device of FIG. 5A.

FIGS. 5A and 5B illustrate another specific exemplary embodiment of an actuation device 500. The actuation device 500 includes a housing 502 that is configured to be grasped by a user during a vascular surgical procedure. The housing 502 couples to an introducer sheath (shown elsewhere) at a first end 504. The introducer sheath translatably carries a catheter (shown elsewhere), and the catheter extends through the housing 502 and outwardly from a port at a second end 508 (for example, to facilitate coupling the catheter to a laser generator). The housing 502 translatably carries a movement actuator, more specifically an arm (not shown), that is coupled to the catheter within the housing 502. The housing 502 further carries a liquid reservoir, more specifically a syringe chamber 510, that carries a liquid and is in fluid communication with the introducer sheath. The syringe chamber 510 translatably carries a liquid infusion actuator, more specifically a piston 512. The piston 512 and the arm both couple to a user input, more specifically a trigger 514, that is actuated by translating toward the second end 508 of the housing 502. As such, actuation of the trigger 514 causes simultaneous movement of the catheter relative to the introducer sheath within the treatment space (specifically, proximally relative to the introducer sheath) and delivery of the liquid from the syringe chamber 510 to the treatment space via the introducer sheath. In some embodiments and as illustrated, the housing 502 may be shaped such that the actuation device 500 generally has an elongated syringe-like appearance.

Figures 6A, 6B:
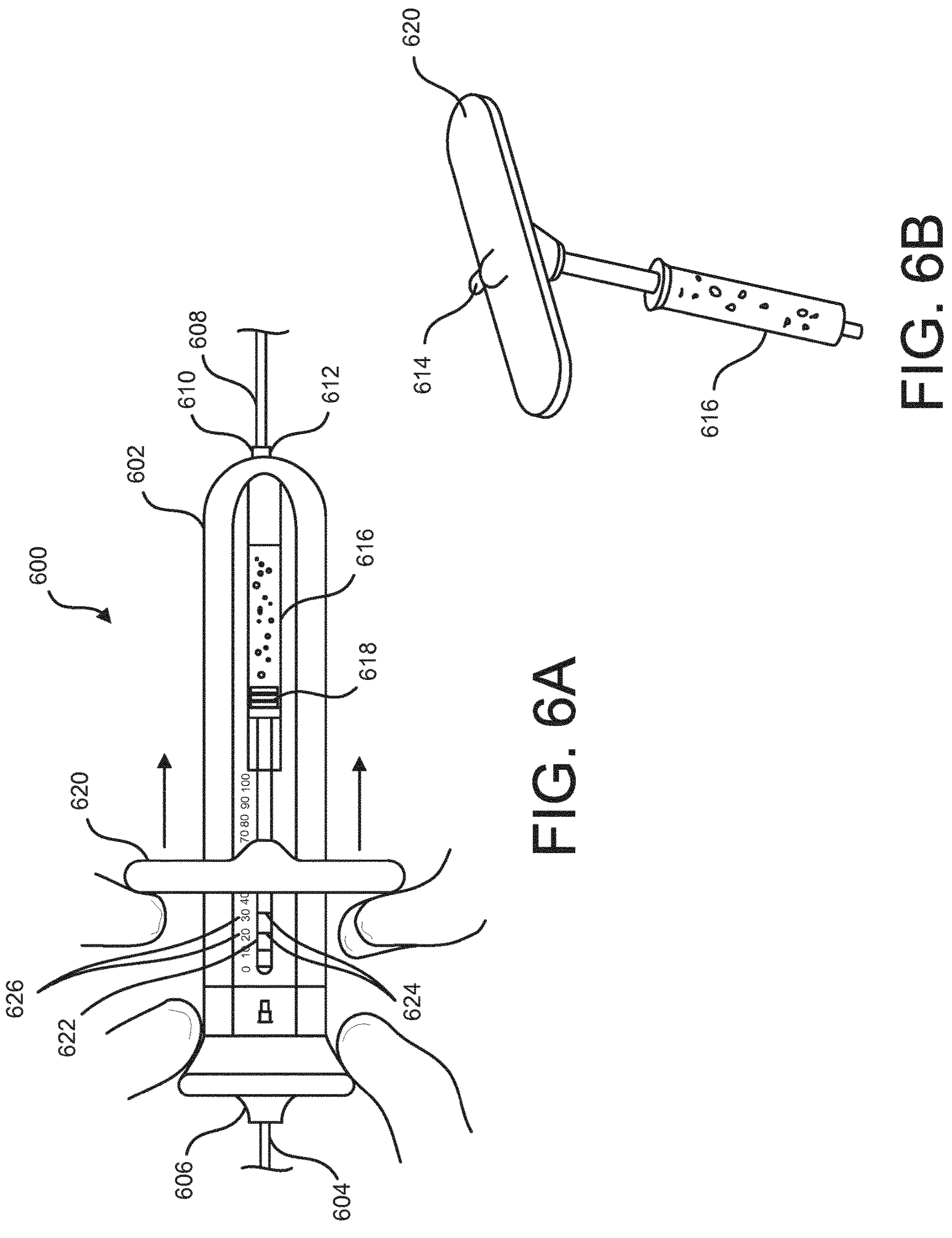
FIG. 6A is a side view of another exemplary actuation device of vascular treatment systems according to embodiments of the present disclosure.
FIG. 6B is a perspective view of a syringe chamber, a piston, a trigger, and an arm of the actuation device of FIG. 6A.

FIGS. 6A and 6B illustrate another specific exemplary embodiment of an actuation device 600. The actuation device 600 includes a housing 602 that is configured to be grasped by a user during a vascular surgical procedure. The housing 602 couples to an introducer sheath 604 at a first end 606. The introducer sheath 604 translatably carries a catheter 608, and the catheter 608 extends through the housing 602 and outwardly from a port 610 at a second end 612 (for example, to facilitate coupling the catheter 608 to a laser generator). The housing 602 translatably carries a movement actuator, more specifically an arm 614 (see FIG. 6B), that is coupled to the catheter 608 within the housing 602. The housing 602 further carries a liquid reservoir, more specifically a syringe chamber 616, that carries a liquid and is in fluid communication with the introducer sheath 604. The syringe chamber 616 translatably carries a liquid infusion actuator, more specifically a piston 618. The piston 618 and the arm 614 both couple to a user input, more specifically a trigger 620, that is actuated by translating toward the second end 612 of the housing 602. As such, actuation of the trigger 620 causes simultaneous movement of the catheter 608 relative to the introducer sheath 604 within the treatment space (specifically, proximally relative to the introducer sheath 604) and delivery of the liquid from the syringe chamber 616 to the treatment space via the introducer sheath 604. In some embodiments, the actuation device 600 includes an indicator for indicating the position of the distal end of the catheter 608. For example and as illustrated, the indicator may include an opening 622 that shows the position of the trigger 620 relative to a plurality of demarcations 624 and indicia 626. In some embodiments and as illustrated, the housing 602 may be shaped such that the actuation device 600 generally has an elongated syringe-like appearance.

Figure 7:
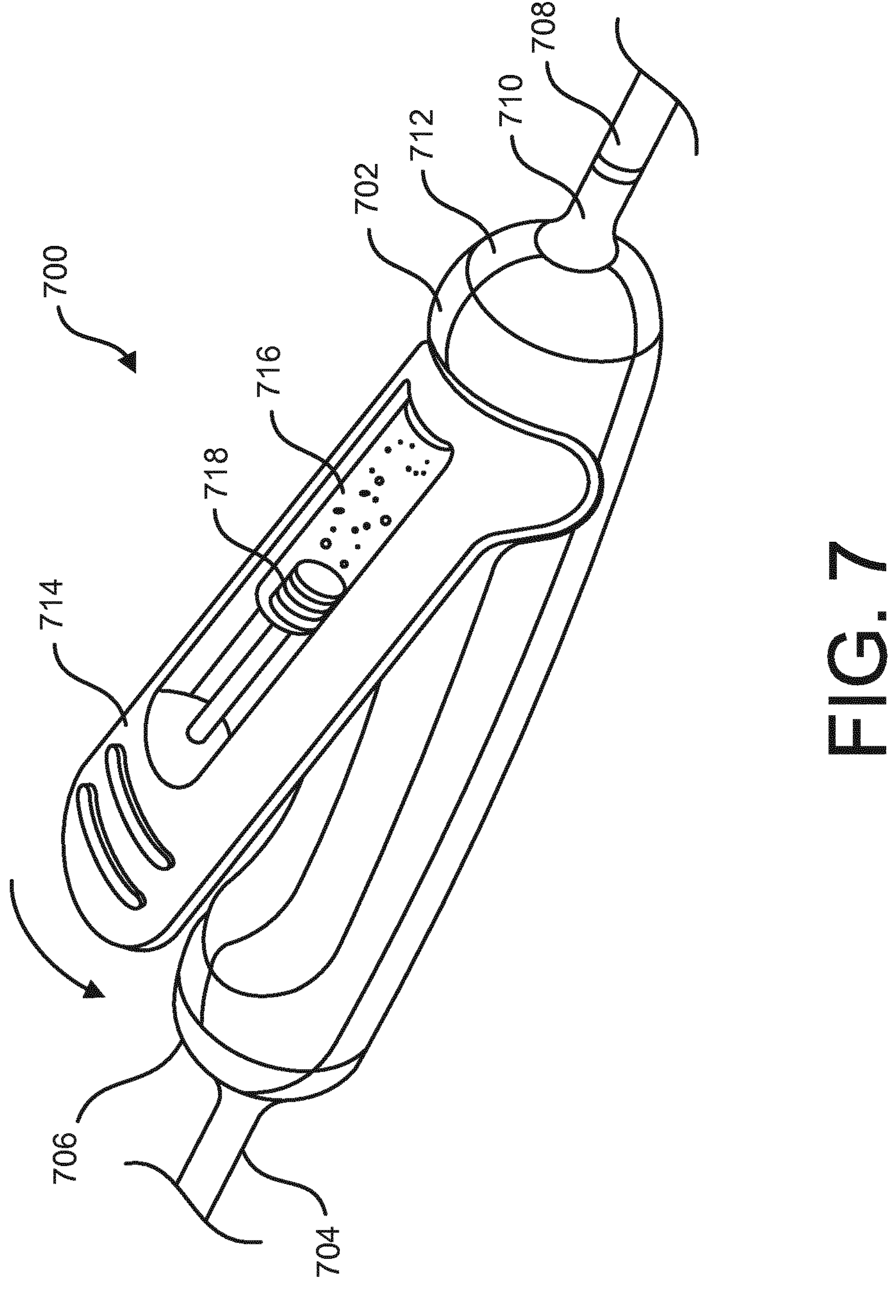
FIG. 7 is a perspective view of yet another exemplary actuation device of vascular treatment systems according to embodiments of the present disclosure.

FIG. 7 illustrates another specific exemplary embodiment of an actuation device 700. The actuation device 700 includes a housing 702 that is configured to be grasped by a user during a vascular surgical procedure. The housing 702 couples to an introducer sheath 704 at a first end 706. The introducer sheath 704 translatably carries a catheter 708, and the catheter 708 extends through the housing 702 and outwardly from a port 710 at a second end 712 (for example, to facilitate coupling the catheter 708 to a laser generator). The housing 702 carries a user input, specifically a rotatable lever 714. The lever 714 carries a liquid reservoir, more specifically a syringe chamber 716, that carries a liquid and is in fluid communication with the introducer sheath 704. The syringe chamber 716 translatably carries a liquid infusion actuator, more specifically a piston 718. The housing 702 translatably carries a movement actuator, more specifically an arm (not shown), that is coupled to the lever 714 and the catheter 708 within the housing 702. As such, actuation of the lever 714 (that is, rotation of the lever 714 relative to the housing 702) causes simultaneous movement of the catheter 708 relative to the introducer sheath 704 within the treatment space (specifically, proximally relative to the introducer sheath 704) and delivery of the liquid from the syringe chamber 716 to the treatment space via the introducer sheath 704. More specifically, the actuation device 700 could include a ratcheting mechanism (not shown) where the piston 718 is advanced toward the hinge of the lever 714 by a certain distance with each actuation of the lever 714. This action would pressurize the liquid in the syringe chamber 716 and thereby deliver the liquid to the catheter. Alternatively, the orientation of the piston 718 and the syringe chamber 716 could be inverted, and the piston 718 could be directly linked into the hinge of the lever 714 and arranged to be pushed or pulled with each actuation of the lever 714. As another alternative, the piston 718 and the syringe chamber 716 could be disposed within the housing 702, and the lever 714 could be arranged to act upon the piston 718 by converting rotation of the lever 714 to a linear incremental motion (for example, by a rack and pinion; not shown) and indexed to only advance in one direction. As yet another alternative, the chamber 716 could be compliant or compressible such that mechanical pressure exerted on the chamber 716 would pressurize the liquid. In these embodiments and others, the lever 714 couples to an off-hinge linking arm (not shown), which linearly actuates the piston 718 upon rotation of the lever 714. The piston 718 may thereby deliver a pressurized fluid (for example, air) to an actuation chamber (not shown) via a one-way pressure valve (not shown). The actuation chamber may thereby expand, engage the chamber 716, and cause the chamber 716 to deliver the liquid to the catheter.

In some embodiments, certain features of the systems and devices described herein may be designed to facilitate delivering liquid at an appropriate flow rate relative to a catheter's translation rate. For example, diameters of a syringe chamber and a piston may be selected to facilitate delivering liquid at an appropriate flow rate relative to a catheter's translation rate.

In the embodiments described above, the liquid delivery rate is fixed relative to a catheter's translation rate. In other embodiments, the liquid delivery rate may be variable relative to a catheter's translation rate.

In the embodiments described above, catheters advance proximally upon actuation of actuation devices. In other embodiments, catheters advance distally upon actuation of actuation devices.

In the embodiments described above, liquid reservoirs are carried by actuation devices. In other embodiments, liquid reservoirs deliver liquids to actuation devices but are not carried by, or are disposed externally from, actuation devices. In these embodiments and others, actuation devices may include valves to facilitate coupling to liquid reservoirs, and liquid reservoirs could be pressurized.

In the embodiments described above, systems and devices include and/or are used together with laser catheters. In other embodiments, systems and devices according to the present disclosure may include and/or may be used together with other types of catheters. For example, such catheters could emit other types of electromagnetic energy (for example, radio-frequency energy) to treat tissues and/or other materials within a treatment space, or such catheters could operate without emitting electromagnetic energy to treat tissues and/or other materials within a treatment space. As a more specific example, some catheters could include cutting elements that physically engage and treats tissue and/or other materials in the treatment space. In some embodiments, systems and devices according to the present disclosure may include and/or may be used together with rotational atherectomy catheters. In some embodiments, systems and devices according to the present disclosure may include and/or may be used together with orbital atherectomy catheters. In some embodiments, systems and devices according to the present disclosure may include and/or may be used together with intravascular imaging catheters. In some embodiments, systems and devices according to the present disclosure may include and/or may be used together with catheters in which a portion or all of a catheter tip or body can rotate relative to other portions of a catheter and/or an introducer or delivery sheath; in these embodiments, the liquid may be a lubricant that facilitates rotation of the catheter.

In some embodiments, movement actuators of systems and devices according to embodiments of the present disclosure may include transmissions or speed reducers.

In some embodiments, user inputs of systems and devices according to embodiments of the present disclosure may take other forms. For example, a user input may be a wheel that is rotatably carried by a housing of the actuation device, and the wheel may be rotatably actuatable relative to the housing to simultaneously actuate the movement actuator and the liquid infusion actuator.

In some embodiments, systems and devices according to the present disclosure may include a chamber (not shown) that is configured such that actuation of the user input produces a negative pressure in the chamber that facilitates aspiration of fluid/materials from the subject.

In some embodiments, systems, devices, and methods according to the present disclosure can incorporate sealing control devices and methods such as those described in U.S. Application Ser. No. 62/728,004, filed Sep. 6, 2018, entitled Valved Handle Assembly Having a Movable Ring, which is hereby incorporated herein by reference in its entirety for all that it teaches and for all purposes.

In the embodiments described above, systems and devices according to the present disclosure are generally mechanical. In other embodiments, systems and devices according to the present disclosure may be electromechanical. More specifically, systems and devices according to the present disclosure may include one or more components that are electrically coupled or non-mechanically operatively coupled to each other.

In some embodiments, systems according to the present disclosure can be provided to a user (for example, a surgeon) in a "ready to use" configuration (that is, without requiring assembly on the part of the user), such as the system 100 shown in FIG. 1. In some embodiments, systems according to the present disclosure can be provided to a user in a disassembled configuration, for example, to permit the user to couple an actuation device to an appropriate vascular treatment device for a particular subject and/or procedure.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A vascular treatment system, comprising:
a vascular treatment device configured to be disposed within a treatment space of a subject;
an actuation device operatively coupled to the vascular treatment device, the actuation device comprising:
a movement actuator operatively coupled to the vascular treatment device, the movement actuator being actuatable to move at least a portion of the vascular treatment device in a proximal direction within the treatment space;
a liquid reservoir carrying a liquid;
a liquid infusion actuator operatively coupled to the liquid reservoir, the liquid infusion actuator being actuatable to deliver the liquid from the liquid reservoir to the treatment space in a distal direction via the vascular treatment device; and
a user input being actuatable to simultaneously actuate the movement actuator and the liquid infusion actuator.

2. The vascular treatment system of claim 1, wherein the vascular treatment device comprises:
an introducer sheath having an inner lumen; and
a catheter translatably carried in the inner lumen of the introducer sheath.

3. The vascular treatment system of claim 2, wherein the catheter is a laser catheter.

4. The vascular treatment system of claim 2, wherein the catheter comprises a distal end configured to be disposed in the treatment space, and the actuation device further comprises an indicator configured to indicate a position of the distal end of the catheter relative to the actuation device.

5. The vascular treatment system of claim 1, wherein the actuation device further comprises a housing, the user input is a trigger, and the trigger is translatably actuatable relative to the housing to simultaneously actuate the movement actuator and the liquid infusion actuator.

6. The vascular treatment system of claim 5, wherein the movement actuator comprises an arm coupling the trigger to the vascular treatment device.

7. The vascular treatment system of claim 1, wherein the actuation device further comprises a housing, the user input is a lever, and the lever is rotatably actuatable relative to the housing to simultaneously actuate the movement actuator and the liquid infusion actuator.

8. The vascular treatment system of claim 1, wherein the liquid reservoir comprises a syringe chamber carrying the liquid, and the liquid infusion actuator comprises a piston movably carried within the syringe chamber.

9. An actuation device for a vascular treatment system, the actuation device comprising:
a movement actuator configured to be operatively coupled to a vascular treatment device, the movement actuator being actuatable to move at least a portion of the vascular treatment device in a proximal direction within a treatment space of a subject;
a liquid reservoir carrying a liquid;
a liquid infusion actuator operatively coupled to the liquid reservoir, the liquid infusion actuator being actuatable to deliver the liquid from the liquid reservoir to the treatment space in a distal direction via the vascular treatment device; and
a user input being actuatable to simultaneously actuate the movement actuator and the liquid infusion actuator.

10. The actuation device of claim 9, further comprising an indicator configured to indicate a position of the vascular treatment device relative to the actuation device.

11. The actuation device of claim 9, further comprising a housing, wherein the user input is a trigger, and the trigger is translatably actuatable relative to the housing to simultaneously actuate the movement actuator and the liquid infusion actuator.

12. The actuation device of claim 11, wherein the movement actuator comprises an arm configured to couple the trigger to the vascular treatment device.

13. The actuation device of claim 9, further comprising a housing, wherein the user input is a lever, and the lever is rotatably actuatable relative to the housing to simultaneously actuate the movement actuator and the liquid infusion actuator.

14. The actuation device of claim 9, wherein the liquid reservoir comprises a syringe chamber carrying the liquid, and the liquid infusion actuator comprises a piston movably carried within the syringe chamber.

15. A vascular treatment system, comprising:
a vascular treatment device configured to be disposed within a treatment space of a subject;
an actuation device operatively coupled to the vascular treatment device, the actuation device comprising:
a movement actuator operatively coupled to the vascular treatment device, the movement actuator being actuatable to move the vascular treatment device in a proximal direction within the treatment space;
a liquid infusion actuator configured to operatively couple to a liquid reservoir, the liquid infusion actuator being actuatable to deliver a liquid from the liquid reservoir to the treatment space in a distal direction via the vascular treatment device; and
a user input being actuatable to simultaneously actuate the movement actuator and the liquid infusion actuator.

16. An actuation device for a vascular treatment system, the actuation device comprising:
a movement actuator configured to be operatively coupled to a vascular treatment device, the movement actuator being actuatable to move the vascular treatment device in a proximal direction within a treatment space of a subject;
a liquid infusion actuator configured to operatively couple to a liquid reservoir, the liquid infusion actuator being actuatable to deliver a liquid from the liquid reservoir in a distal direction to the treatment space via the vascular treatment device; and
a user input being actuatable to simultaneously actuate the movement actuator and the liquid infusion actuator.

* * * * *